(12) United States Patent
Bridges et al.

(10) Patent No.: US 7,014,781 B2
(45) Date of Patent: Mar. 21, 2006

(54) METHODS AND ARTICLES FOR MAINTAINING HYDANTOINYLATED POLYMERS IN A BIOCIDALLY ACTIVE STATE

(75) Inventors: Michael A. Bridges, Seattle, WA (US); Hiroyuki Kawai, Kirkland, WA (US); Tay-Yuan Chen, Bellevue, WA (US); Everett J. Nichols, Edmonds, WA (US); Jeffrey F. Williams, Langley, WA (US); Steven McClure, Seattle, WA (US); Jerry Wetherbee, Port Ludlow, WA (US)

(73) Assignee: Vanson Halosource, Inc., Redmond, WA (US)

( * ) Notice: Subject to any disclaimer, the term of this patent is extended or adjusted under 35 U.S.C. 154(b) by 0 days.

(21) Appl. No.: 11/180,280

(22) Filed: Jul. 12, 2005

(65) Prior Publication Data

US 2005/0249694 A1    Nov. 10, 2005

Related U.S. Application Data

(62) Division of application No. 10/951,282, filed on Sep. 27, 2004.

(60) Provisional application No. 60/507,735, filed on Oct. 1, 2003.

(51) Int. Cl.
| | |
|---|---|
| C02F 1/76 | (2006.01) |
| C08F 122/40 | (2006.01) |
| C08F 126/06 | (2006.01) |
| C08F 22/40 | (2006.01) |
| A01N 33/14 | (2006.01) |

(52) U.S. Cl. .................. 210/754; 525/326.8; 525/282; 525/355; 525/356; 525/357; 525/358; 424/78.36; 424/405; 252/187.33; 252/187.34; 210/753; 210/756; 210/199; 210/200; 210/210; 210/206; 422/37

(58) Field of Classification Search ................... 422/37; 525/326.8
See application file for complete search history.

(56) References Cited

U.S. PATENT DOCUMENTS

| | | | | |
|---|---|---|---|---|
| 3,446,893 | A | * | 5/1969 | Hanford et al. ............. 424/76.3 |
| 3,629,408 | A | * | 12/1971 | Horvath et al. ............. 424/665 |
| 3,647,523 | A | * | 3/1972 | Horvath et al. ............. 423/274 |
| 3,870,471 | A | * | 3/1975 | Tepas et al. ................. 422/106 |
| 3,912,627 | A | * | 10/1975 | Tepas, Jr. .................... 210/707 |
| 4,888,118 | A | * | 12/1989 | Barnes et al. |
| 5,176,836 | A | * | 1/1993 | Sauer |
| 5,213,884 | A | * | 5/1993 | Fellows ...................... 442/263 |
| 5,407,598 | A | * | 4/1995 | Olson et al. |
| 5,490,983 | A | * | 2/1996 | Worley et al. .............. 424/405 |

(Continued)

FOREIGN PATENT DOCUMENTS

WO    WO 01/52651 A1  *  7/2001

(Continued)

Primary Examiner—Joseph D. Anthony
(74) Attorney, Agent, or Firm—Christensen O'Connor Johnson Kindness PLLC

(57) ABSTRACT

A composition and the method for sustaining the biocidal activity of chlorinated polystyrene hydantoin beads. The method comprises supplying a continuous low level halogen concentration to the chlorinated polystyrene hydantoin beads in the water to be treated that flows in contact with the chlorinated polystyrene hydantoin beads, resulting in treated water suitable for drinking.

11 Claims, 4 Drawing Sheets

U.S. PATENT DOCUMENTS

| | | | | |
|---|---|---|---|---|
| 5,670,646 | A | * | 9/1997 | Worley et al. ............ 548/301.1 |
| 5,808,089 | A | * | 9/1998 | Worley et al. ............ 548/318.5 |
| 5,889,130 | A | * | 3/1999 | Worley et al. .............. 526/261 |
| 6,020,491 | A | * | 2/2000 | Wonley et al. .............. 544/220 |
| 6,162,452 | A | * | 12/2000 | Worley et al. .............. 424/405 |
| 6,210,646 | B1 | * | 4/2001 | Larson et al. |
| 6,294,185 | B1 | * | 9/2001 | Worley et al. .............. 424/405 |
| 6,447,722 | B1 | * | 9/2002 | Rakestraw |
| 6,528,466 | B1 | * | 3/2003 | Lan et al. ................... 510/191 |
| 6,548,054 | B1 | * | 4/2003 | Worley et al. ........... 424/78.36 |
| 6,589,443 | B1 | * | 7/2003 | Olson et al. ............. 252/186.2 |
| 6,680,070 | B1 | * | 1/2004 | Howarth et al. |
| 6,749,758 | B1 | * | 6/2004 | Howarth et al. |
| 6,768,009 | B1 | * | 7/2004 | Sun et al. ................ 548/301.1 |
| 6,823,530 | B1 | * | 11/2004 | Quincy, III ...................... 2/67 |
| 6,852,312 | B1 | * | 2/2005 | Worley et al. ........... 424/78.36 |
| 2003/0044377 | A1 | * | 3/2003 | Worley et al. ........... 424/78.22 |
| 2003/0077365 | A1 | * | 4/2003 | Howarth ..................... 426/332 |
| 2003/0144638 | A1 | * | 7/2003 | Quincy ....................... 604/360 |
| 2004/0040915 | A1 | * | 3/2004 | Connelly |
| 2004/0127667 | A1 | * | 7/2004 | Worley et al. ................ 528/10 |

FOREIGN PATENT DOCUMENTS

WO     WO 01/53215 A1 * 7/2001

* cited by examiner

METHODS AND ARTICLES FOR MAINTAINING HYDANTOINYLATED POLYMERS IN A BIOCIDALLY ACTIVE STATE

CROSS-REFERENCE TO RELATED APPLICATION

This application is a divisional of U.S. patent application Ser. No. 10/951,282, filed Sep. 27, 2004, which claims the benefit of U.S. Provisional Patent Application No. 60/507,735, filed Oct. 1, 2003, incorporated herein by reference.

FIELD OF THE INVENTION

The invention is related to water purification systems, including systems employing polymers having pendant heterocyclic amine groups, such as polystyrene having pendant hydantoin and halogenated hydantoin groups, and to the compositions and methods for maintaining the polymers in a biocidally active state.

BACKGROUND OF THE INVENTION

Heterocyclic N-halamine groups are known to have biocidal properties that can be put to use in water purification. Heterocyclic N-halamine groups that are attached to a polystyrene polymer are described in U.S. Pat. No. 5,490,983. A crosslinked polystyrene polymer having similar pendant heterocyclic N-halamine groups is described in U.S. Pat. No. 6,548,054. The crosslinked version of the polystyrene polymer is typically provided in beads that do not have the problems associated with a powder. The beads are available from Vanson HaloSource of Redmond, Wash. A representative heterocyclic amine group described in both of these patents is a hydantoin group. When the hydantoin group has a chlorine or bromine atom bonded to one or both of the hydantoin nitrogen atoms, the hydantoin is biocidal. Worley et al. '054 describe methods for the creation of the biocidal halogenated polystyrene hydantoin (HPSH) polymer from the non-biocidal polystyrene hydantoin (PSH) polymer using a variety of free chlorine sources (for example, sodium hypochlorite, calcium hypochlorite, sodium dichloroisocyanurate). Over time however, the biocidal HPSH polymer reverts to nonbiocidal PSH polymer as a result of depletion of the halogen atoms due to contact with the biodemand. PSH polymer, however, has the ability to be recharged or rehalogenated with a halogen to restore its antimicrobial properties.

Worley et al. '054 describe recharging PSH polymer once the polymer has lost its biocidal efficacy by halogenating the PSH polymer using concentrated solutions of industrial strength liquid bleach and bromine. It has been determined that the levels of halogen in solution according to Worley et al. '054 are of such high concentration that when used in-situ in a water treatment device, the subsequent purified water is rendered undrinkable and requires considerable post-treatment to remove the excess halogen to render the purified water drinkable.

One of the drawbacks of using HPSH polymer in water filters is that once the halogen is consumed from the HPSH polymer, the halogen must be either replaced by recharging the halogen-depleted PSH polymer, or the entire mass of PSH polymer must be discarded and replaced with fresh HPSH polymer. Until now, there was no practical alternative to either recharging or replacing the PSH polymer in a water treatment system. Replacing halogen-depleted PSH polymer with fresh HPSH polymer raises the capital and operating costs of the water treatment system. Recharging PSH polymer that has lost biocidal efficacy requires that the water treatment system be taken out of service. Off-line recharging of PSH polymer to HPSH polymer creates considerable down-time and system complexity.

Another short-coming of HPSH polymers is the drop in biocidal efficacy during use. As halogen is consumed from the HPSH polymer, the biocidal efficacy of the HPSH polymer drops below commonly required biocidal performance standards, such as the United States Environmental Protection Agency (EPA) purifier standards of 6 log removal of *Klebsiella*, and 4 log removal of poliovirus. While the drop in biocidal efficiency is expected as halogen is consumed by the biodemand, the speed at which this reduced effectiveness occurs creates several difficulties for the practical application of the HPSH polymer in applications, such as a water filter in the home or as an emergency water supply. Product designers and engineers wishing to apply HPSH polymer technology to commercial products must either increase the initial amount of HPSH polymer to achieve the desired performance life of the product or add complexity to the system by allowing for off-line rehalogenation of the PSH polymer.

Accordingly, there is a need to provide methods and the means to maintain constantly or for a prolonged period of time, a biocidally effective halogen charge on polymers having pendant heterocyclic N-halamine groups without adversely affecting water quality, and without the need to recharge or replace the halogen depleted PSH polymer. The present invention fulfills this need and has further related advantages.

SUMMARY OF THE INVENTION

In accordance with the present invention, the need for replacing the halogen-depleted charge of HPSH polymer with new HPSH polymer or taking a water treatment system off-line for recharging, is avoided by providing a low concentration of halogen in the water that is to be treated that is sufficient to maintain the HPSH polymer at an effective biocidally active state. Ideally, the concentration is sufficient to maintain the HPSH polymer biocidal, yet not so high as to render the treated water undrinkable due to high concentrations of halogen. In this manner, the HPSH polymer is constantly maintained at an effective biocidal level, thus eliminating replacement or recharging. However, one of the difficulties of implementing this new solution is in achieving a prolonged low concentration of free halogen in water to bond with the heterocyclic amines to render them biocidal, yet not have the halogen concentration so high as to adversely effect water potability.

Up until now, commercially available solid sources of halogens are designed for use in an emergency to provide drinking water and/or for pool and spa sanitizing. Examples of solid halogen sources include calcium hypochlorite tablets for municipal drinking water system disinfection, bromine tablets for pool and spa sanitation, and sodium dichloroisocyanurate tablets for disaster relief/emergency water treatment. However, these commercially available sources of halogens elute free halogens at concentrations far greater than would be accepted by consumers for drinking water. Worley et al. '983 and '054 does not mention or indicate the halogen concentration in water required to maintain a biocidally active state of the HPSH polymer that would still be low enough so that the water is suitable for use as potable water. Furthermore, no mention of a means for continuously maintaining or least prolonging the biocidally active state of HPSH polymer is described. Worley et al. '983 only describe the regeneration of non-halogenated precursor cyclic amine polymers in filters.

In accordance with the present invention of prolonging the biocidally active state of polymers having pendant heterocyclic amine groups, the present invention provides methods and the means to maintain continuously or for a prolonged period of time a low concentration of free halogen in water to maintain or prolong the effective halogen loading on polymers having pendant heterocyclic amines. The present invention avoids the need to recharge the polymers after they have become biocidally ineffective and also avoids the need to take a water purification system off-line for recharging biocidally ineffective polymers. With the use of the present invention, the polymers having pendant heterocyclic amine groups are maintained biocidally effective constantly or for at least prolonged periods of time. The present invention treats the polymers having pendant heterocyclic amine groups with low concentrations of free halogen in water while the polymer is still biocidally effective. Free halogen refers to the halogen in water that is available to bond with a nitrogen atom on a heterocyclic amine. The present invention provides halogens to bond with nitrogen atoms on the heterocyclic amine groups, simultaneously while halogens are being depleted from the heterocyclic amine groups by the biodemand, so that the polymer with pendant heterocyclic amines is not rendered biocidally ineffective. Thus, the need to recharge the polymer from a biocidally ineffective state is avoided. It is to be appreciated that the heterocyclic amine groups may have halogen depleted sites.

In one embodiment of the invention, an article is designed and manufactured to provide free halogen at low concentrations for prolonged periods of time for use in water treatment systems employing polymers having pendant heterocyclic N-halamines, such as hydantoin moieties. The article according to the present invention can elute free halogen into a flowing water stream that then contacts the polymer with pendant heterocyclic N-halamines to maintain an effective halogen loading of the polymer so that the polymer achieves a continuous or at the very least a prolonged period of biocidal activity without the need to replace the entire mass of halogen-depleted polymer and without the need to take the system off-line for recharging the biocidally ineffective halogen-depleted polymer. The article according to the invention allows for on-line, in-situ halogenation of the biocidally effective polymer during the period when the polymer is biocidally active. The article achieves maintenance of the effective halogen loading on the polymer by releasing a low level dose of halogen into flowing water to create a solution having a total free chlorine concentration in the range of about 0.1 ppm to about 3 ppm and/or a total free bromine concentration in the range of about 0.2 ppm to about 4 ppm. The lower limit of these ranges is still effective to produce a biocidally active polymer having pendant hydantoin groups. The higher limit of these ranges still produces a biocidally active polymer having pendant hydantoin groups, but is not so high as to render water nonpotable. "Nonpotable", "not suitable for drinking", or "undrinkable" refers to water having chlorine or bromine or both chlorine and bromine at a concentration such that a majority of a population would avoid drinking the water if the population has an abundant alternate water supply. The water with the low concentration of free halogen within these ranges is then made to contact the polymer with pendant heterocyclic N-halamine groups, continuously or intermittently.

In one embodiment, the article of the invention is a solid, monolithic tablet that elutes chlorine or bromine within predetermined limits into untreated flowing water that is subsequently exposed to a biocidally active polymer having pendant heterocyclic N-halamine groups. The method and article according to the invention achieve the constant or prolonged biocidally active state of polymers having pendant heterocyclic N-halamines by replacing the halogens that are constantly being depleted by the biodemand. This is in direct contrast to Worley et al. '983 and '054 that only recharges the polymer after the polymer has been depleted of halogen that has rendered the polymer biocidally ineffective. With the article according to the invention, the biocidally active state of any polymer having pendant heterocyclic N-halamine groups can be maintained continuously or at the very least for a prolonged period of time as compared with the prior art that only recharges the polymer after the polymer has been rendered biocidally inactive.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
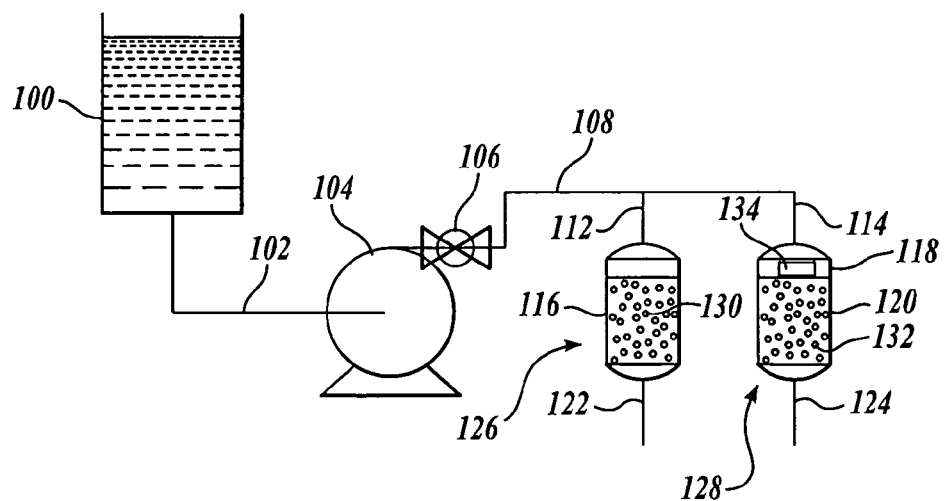
FIG. 1 is a schematic illustration of a system for measuring the concentrations of halogen in water flowing past an article made according to the present invention.

The present invention is related to methods and the means for maintaining a prolonged biocidally active state for polymers having pendant heterocyclic N-halamine groups. Specifically, one embodiment of the present invention provides an article for maintaining a continuous long-term level of biocidal efficacy for water treatment devices that employ hydantoinylated polymers, such as PSH polymer, HPSH polymer, and/or a mixture of PSH polymer and HPSH polymer.

The article according to the present invention elutes low concentrations of free halogen into the water that is to be treated by a water treatment device that includes HPSH polymer. One representative article of the invention is a solid phase composition including at least a source of chlorine, bromine, or both chlorine and bromine. The article is provided as a monolithic composition, meaning the article has no layers of differing compositions or, stated another way, the article is substantially homogeneous with regard to composition. The article according to the invention has been designed and manufactured in a manner as set forth below to elute free halogen at the desirable predetermined concentration into water.

It is believed the predetermined concentration of free halogen eluted by the article is attributable, at least in part, to the method of its manufacture that includes taking into consideration the article's size, shape, density and its components. The article according to the present invention produces a total free chlorine concentration in the range of about 0.1 ppm to about 10 ppm, and preferably in the range of about 0.1 ppm to about 3 ppm and/or a total bromine concentration in the range of about 0.1 ppm to about 10 ppm, and preferably in the range of about 0.2 ppm to about 4 ppm in a flowing water stream averaging from about 10 ml/min. to about 3 liter/min, and preferably from about 10 ml/min to about 250 ml/min, averaged over a total flow of about 10 liters to about 150 liters. However, it is to be appreciated that the article according to the invention can produce chlorine or bromine or both chlorine and bromine for much larger total volumes of water flow. The low concentration of chlorine and/or bromine in water by itself is insufficient to achieve the 4-log and 6-log removal standards required by the EPA. However, this low concentration of chlorine and/or bromine when supplied in the untreated water is sufficient to sustain a HPSH polymer at a biocidally effective level that is able to achieve the required 4-log and 6-log removal rate.

One embodiment for making the article includes reconstituting commercially available compounds by either crushing the commercial products into a powder or obtaining powdered versions of the compounds. The powder or powders can be passed through sieves of various sizes to obtain the appropriate sized grains. The powder or powders can be combined, optionally with one or more other sources of chlorine or bromine or adjuvants, in predetermined amounts, and fully mixed together. The mixture is compressed by any commercial tablet manufacturing apparatus to achieve an article of a certain density, size, or shape. Depending on the amount of compaction, the size, shape, or density of the article, the concentrations of chlorine or bromine or both eluted from the article, can be affected. For example, the article according to the invention can have a density that is in the range of from about 1.4 grams per cubic centimeter to about 4 grams per cubic centimeter.

The article according to the invention includes one or more compounds capable of releasing chlorine and/or bromine at predetermined low concentrations in flowing or stagnant water that is determined by the design of the article, including the article's solubility, density, erosion rate, ratio of volume to surface area, and optionally, the amount and/or type of binders and tableting aides. Low when referring to the concentration of a halogen in water means about 0.1 ppm by weight to about 3 ppm by weight chlorine and about 0.2 ppm by weight to about 4 ppm by weight bromine. Depending on the desired level of free halogen required to maintain a biocidally active HPSH polymer, one or more of the variable factors mentioned herein can be adjusted. Optional adjuvants, tableting and compaction aides include calcium phosphate, dicalcium phosphate, tricalcium phosphate, sodium bicarbonate, a polyfluorinated polymer, lactose, a fatty acid, a wax, calcium stearate, magnesium stearate, talc, starch, calcium carbonate, sucrose, glucose, mannitol, sorbitol, bentonite, carboxymethylcellulose, methylcellulose, hydroxyethylcellulose, hydroxypropylcellulose, sodium metaphosphate, magnesium oxide, polytetrafluoroethylene (TEFLON®7), polyfluorinated polymers, phosphate buffers, sodium based phosphate buffers, dibasic sodium phosphate, monobasic sodium phosphate, tribasic sodium phosphate, sodium hexametaphosphate, potassium based phosphate buffers, dibasic potassium phosphate, monobasic potassium phosphate, or any combinations. The tableting and compaction aides are preferably selected to be compatible with the source of halogen. Sources of chlorine and bromine can include, but are not limited to the following.

1. A halohydantoin, including but not limited to 1,3, dichloro-5,5-dimethylhydantoin 1,3,dibromodimethylhydantoin, 1-chloro-3-bromo-5,5-dimethylhydantoin or 1-bromo-3-chloro-5,5-dimethylhydantoin;

2. A chlorinated isocyanurate or a metal salt of a chlorinated isocyanurate, including but not limited to trichloroisocyanuric acid, dichloroisocyanuric acid, potassium trichloroisocyanurate, sodium trichloroisocyanurate, potassium dichloroisocyanurate or sodium dichloroisocyanurate;

3. A N-halooxazolidinone, including but not limited to 3-chloro-2,2-dialkyl-4,4-dimethyl-1,3-oxazolidinone, 3-chloro-4,4-dimethyl-2-oxazolidinone, 3-bromo-4,4-dimethyl-2-oxazolidinone, 3-chloro-4-ethyl-4-methyl-2-oxazolidinone, 3-bromo-4-ethyl-4-methyl-2-oxazolidinone, 3-chloro-4-methyl-2-oxazolidinone, 3-bromo-4-methyl-2-oxazolidinone, or 3-chloro-2-oxazolidinone, or 3-bromo-2-oxazolidinone;

4. A N,N'-dihaloimidazolidinone, including but not limited to 1,3-dichloro-4,4,5,5-tetramethyl-2-imidazolidinone, 1,3-dibromo-4,4,5,5-tetramethyl-2-imidazolidinone, 1-bromo-3-chloro-4,4,5,5-tetramethyl-2-imidazolidinone, 1,3-dichlor-2,2,5,5-tetramethyl-4-imidazolidinone, 1,3-dibromo-2,2,5,5-tetramethyl-4-imidazolidinone, or 1-bromo-3-chloro-2,2,5,5-tetramethyl-4-imidazolidinone;

5. A N-halosuccinimide, including but not limited to N-chlorosuccinimide or N-bromosuccinimide;

6. A N-halomelamine, including but not limited to trichloromelamine;

7. A N-haloglycoluril, including but not limited to tetrachloroglycoluril tetrachlorodimethylglycoluril, tetrabromoglycoluril or tetrabromodimethylglycoluril;

8. A sulfonhalamide, including but not limited to sodium p-toluenesulfonchloramide (chloramine T), p-toluenesulfondichloramide (dichloramine T), sodium benzenesulfonchloramide (chloramine B), p-sulfondichloramidobenzoic acid, N-chloro-N-methyl-p-toluenesulfonamide, sodium p-toluenesulfonbromamide (bromoamine T), p-toluenesulfondibromoamide (dibromamine T), sodium benzenesulfonbromoamide (bromamine B), p-sulfondibromamidobenzoic acid or N-bromo-N-methyl-p-toluenesulfonamide;

9. A cyclic N-halamine, including but not limited to 1,3,5-trichloro-2,4-dioxohexahydrotriazine, 1,3,5-tribromo-2,4-dioxohexahydrotriazine, 1-chloro-2,2,6,6-tetramethylpiperidine, 1-bromo-2,2,6,6-tetramethylpiperidine, 1,4-dichloro-2,2,5,5-tetramethyl-3,6-piperazinedione, 1,4-dibromo-2,2,5,5-tetramethyl-3,6-piperazinedione, 1-chloro-2,2,6,6-tetramethyl-4-piperidone or 1-bromo-2,2,6,6-tetramethyl-4-piperidone;

10. An acyclic N-halamine, including but not limited to N,N'-dichloroazodicarbonamidine (Chloroazodin) or N,N'-dibromoazodicarbonamidine;

11. A solid metal salt of hypochlorous acid, including but not limited to calcium hypochlorite or lithium hypochlorite;

12. A metal salt of hypobromous acid, including but not limited to calcium hypobromite, sodium hypobromite, lithium hypobromite, or potassium hypobromite;

13. A bromide salt, including but not limited to sodium bromide, lithium bromide, or potassium bromide;

14. A chloride salt, including but not limited to sodium chloride, lithium chloride, or potassium chloride;

15. Sodium hypochlorite;

16. A metal salt of oxychlorosene, including but not limited to sodium oxychlorosene.

The grain size, tablet dimensions, density, and relative percentages of halogen source to other potential materials in the article are adjusted based on the desired level of halogen needed for the particular water purification system employing the HPSH polymer. The hydraulic characteristics of the water purification system can also be taken into account. Tests can be easily conducted to achieve the desired concentrations of halogen for each particular water purification system to determine the proper amounts of the chlorine and or bromine source compounds, as well as the size, shape, density, and surface area of the article.

For one particular embodiment of a water purification system, the following ratios provided the desired halogen concentrations. The list is not exhaustive and it is to be appreciated that ratios can deviate from the following depending on the chosen water purification system and the other variable factors affecting the article. All ratios are given as weight ratios. For an article comprising trichloromelamine and magnesium oxide, the ratio of the respective compounds is about 1:1. For an article comprising dichlorodimethylhydantoin, sodium metaphosphate and polytetrafluoroethylene (TEFLON®7), the ratio of the respective compounds is about 2:2:1. For an article comprising calcium hypochlorite and polytetrafluoroethylene (TEFLON®7), the ratio of the compounds is about 1:3. For an article comprising sodium dichloroisocyanurate, calcium phosphate dibasic, and polytetrafluoroethylene (TEFLON®7), the ratio of the respective compounds is about 1:1:2. For an article comprising sodium trichloroisocyanurate, sodium metaphosphate, and polytetrafluoroethylene (TEFLON®7), the ratio of the respective compounds is about 2:1:4.

In one embodiment, a composition comprising trichloromelamine, a buffer and sodium bicarbonate, is provided. The composition can be compressed into a tablet that provides chlorine in the range of about 0.1 to about 3 ppm in a flowing water stream. The buffer can include sodium based phosphate buffers or potassium based phosphate buffers. Sodium based phosphate buffers include dibasic sodium phosphate, monobasic sodium phosphate, tribasic sodium phosphate, and sodium hexametaphosphate. The potassium based phosphate buffers include dibasic potassium phosphate and monobasic potassium phosphate. For an article comprising trichloromelamine, a buffer and sodium bicarbonate, the amounts of the respective compounds are the following: trichloromelamine is about 25% to about 85% by weight, buffer is about 1% to about 50% by weight, and sodium bicarbonate is about 0.5% to about 33% by weight. In one embodiment, an article comprising trichloromelamine, sodium hexametaphosphate and sodium bicarbonate the ratio of the respective compounds is about 2:1:0.2.

Suitable polymers that can be used in combination with the article of the invention, include any polymer that can be rendered biocidal on contact with water to be treated that includes free halogen at a concentration generated by the article. For example, polymers having heterocyclic amine groups that can be halogenated with the article of the invention. One representative heterocyclic amine group is a hydantoin moiety. Hydantoins along with several other heterocyclic amine groups and the polymers incorporating these compounds are described in U.S. Pat. Nos. 5,490,983 and 6,548,054; and U.S. Published Application No. 10/400,165, all of which are incorporated herein by reference.

In another aspect, the invention provides a method for sustaining the biocidal efficacy of polymers having pendant heterocyclic N-halamines. The method relies on a water purification device having two compartments, one respectively for an article of the invention, and the other for a polymer having pendant heterocyclic N-halamines. The compartments are in communication with each other such that water to be treated passes into and out of the first compartment with an article and is then directed to flow into and out of the second compartment with the polymer having pendant heterocyclic N-halamines. The polymer is situated downstream from an article according to the invention. The polymer is located in the compartment that has a water inlet and outlet. The polymer is situated such that the water contacts the polymer before exiting through the water outlet. A second compartment is provided for an article made in accordance with the invention. The second compartment for the article likewise has a water inlet and outlet. The second compartment is also configured in a manner that induces water to contact the article before the water exits the compartment. The second compartment containing the article is situated such that water to be treated entering the device contacts the second compartment containing the article before contacting the compartment containing the polymer. The water outlet from the article compartment is connected to the water inlet to the polymer compartment. The water purification system may incorporate any other type of filters before or after the article compartment or the polymer compartment. For example, a ceramic filter may be located ahead of the article compartment. Other filters, such as activated carbon filters may also be used. Untreated water or water to be treated, meaning water that has not contacted the polymer, is allowed to enter the article compartment through the water inlet where contact is made with the article. In contacting the article, free chlorine or bromine or both chlorine and bromine are eluted into the water at the concentrations described herein. The halogenated water leaves the article compartment through the water outlet, and enters the polymer compartment through the polymer compartment water inlet. While the halogen is being depleted by the biodemand, the HPSH polymer within the polymer compartment is halogenated by the water. The article according to the invention provides free chlorine or bromine or both chlorine and bromine into the water at specified predetermined concentrations. A further advantage of the article made in accordance with the present invention is the minimal effect on the pH of the water flowing over the article. A small pH increase or pH decrease in the water that passes over the article may be noticed however. A change of about plus or minus one pH unit may sometimes be realized between the water before the article and the water after the article.

FIG. 1 illustrates a representative experimental apparatus used in the determination of free halogen in water from articles made in accordance with the present invention. The experimental apparatus includes a water feed tank 100. The water feed tank 100 contains water that is either untreated or, alternatively, can include municipally treated water. However, municipally "treated" water is considered untreated for purposes of this application, if the water is not treated by passing over a heterocyclic N-halamine polymer. The water feed tank 100 is connected to the suction side of the water feed pump 104. The line 102 connects the water feed tank to the suction side of the water feed pump 104. The water feed pump 104 pumps water through a control valve 106. The control valve 106 meters the amount of water that is pumped by the water feed pump 104 to two chambers 126 and 128. The water from the control valve 106 flows through the line 108. The water from line 108 flows into branch line 112 and branch line 114. Branch line 112 feeds a metered amount of water into the chamber 126 having a polymer compartment 116 but without an article compartment. The compartment 116 is filled with PSH polymer or HPSH polymer beads 130. The chamber 126 is used as the control. Branch line 114 feeds a metered amount of water into the chamber 128 with a polymer compartment 120 and also including an article compartment 118. Compartment 120 is filled with PSH polymer or HPSH polymer beads 132. Compartment 118 includes a replaceable article 134, such as a tablet, made in accordance with the invention. By introducing different articles into the article compartment 118 ahead of the polymer compartment 120, a side-by-side comparison can be made of the levels of halogen loading of the polymer downstream of the article compared with a control sample of the polymer that is not exposed to water containing low concentrations of halogen. The concentration of halogen in the water streams 122 and 124 that exit the chambers 126 and 128 are measured analytically. As can now be more readily understood from the description provided, practical applications for the use of HPSH polymer in water purification systems are made possible by the invention.

Figure 2:
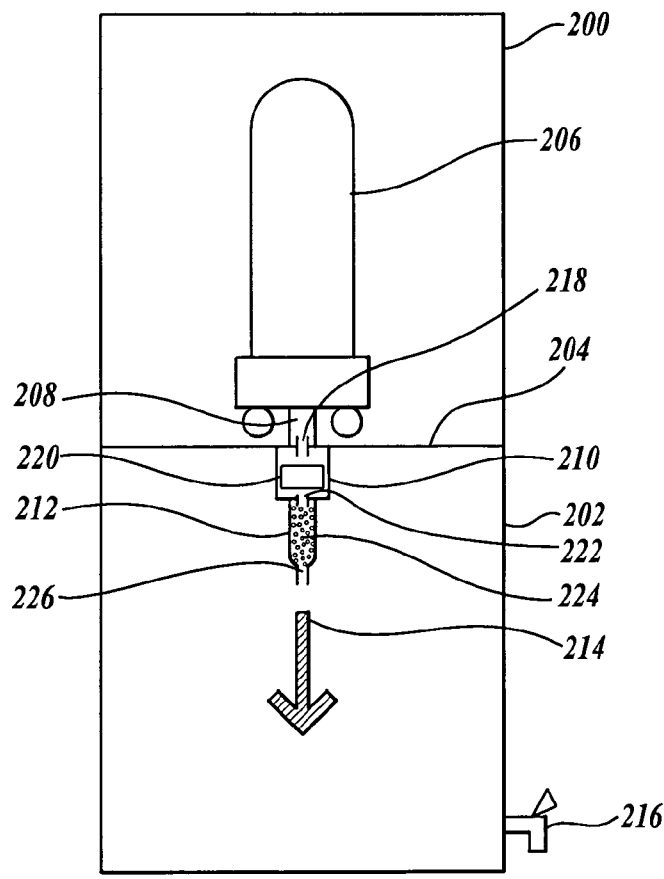
FIG. 2 is a schematic illustration of a representative water purification system incorporating an article made according to the present invention.

Referring to FIG. 2, a gravity feed water purification system having an article for the constant halogenation of HPSH polymer according to the invention is illustrated. The system includes an upper chamber 200 and a lower chamber 202 separated by a horizontal dividing wall 204. The upper chamber 200 contains a flow-through ceramic filter 206 that is connected to a conduit 208 for channeling water from the ceramic filter 206 to the lower chamber 202. The conduit 208 discharges through the dividing wall 204 into an article compartment 210 located in the bottom chamber 202. The article compartment 210 is connected at the conduit outlet 218 so that water exiting the ceramic filter 206 enters and passes through the article compartment 210. The article compartment has an outlet for water leading to the inlet 222 to a polymer compartment 212. The polymer compartment 212 contains the HPSH polymer beads 224. The water purification cartridge described in U.S. patent application Ser. No. 10/676,730, filed on Oct. 1, 2003, can be used in the water purification system of FIG. 2. The water purification cartridge of U.S. patent application Ser. No. 10/676,730 describes a filter having compartments that can be used to contain an article of the present invention and to contain HPSH polymer. U.S. patent application Ser. No. 10/676,730 is incorporated herein by reference.

Untreated water deposited into the upper chamber 200 rises to a level such that the water flows through the ceramic filter 206 and the article compartment 210 before entering the polymer compartment 212. On passing through the article compartment 210, the untreated water contacts the article 220 where the article releases chlorine into the water at the concentrations predetermined to sustain the biocidal efficacy of the HPSH beads, but does not render the water unsuitable for drinking. The water containing the predetermined concentrations of halogen further contacts the HPSH polymer beads 224 in the polymer compartment 212. In this manner, the article 220 in compartment 210 is able to maintain the HPSH polymer beads 224 at a biocidally effective level. Treated water 214 exits the polymer compartment 212 from the polymer compartment outlet 226 accumulates in the lower chamber 202. Water drawn from the lower chamber 202 through faucet 216 is both treated and suitable for drinking. It can be understood that the method according to the invention includes contacting untreated water with a plurality of N-halohydantoin functionalized beads having biocidal activity for a time sufficient to provide water suitable for drinking, wherein the untreated water comprises a contaminant and a halogen. On contact with a contaminant in the water, at least a portion of the plurality of N-halohydantoin functionalized beads are converted to hydantoin functionalized beads to provide an inactive contaminant, while at the same time at least a portion of the hydantoin functionalized beads are converted to N-halohydantoin functionalized beads on contact with the halogen in the untreated water.

Figure 3:
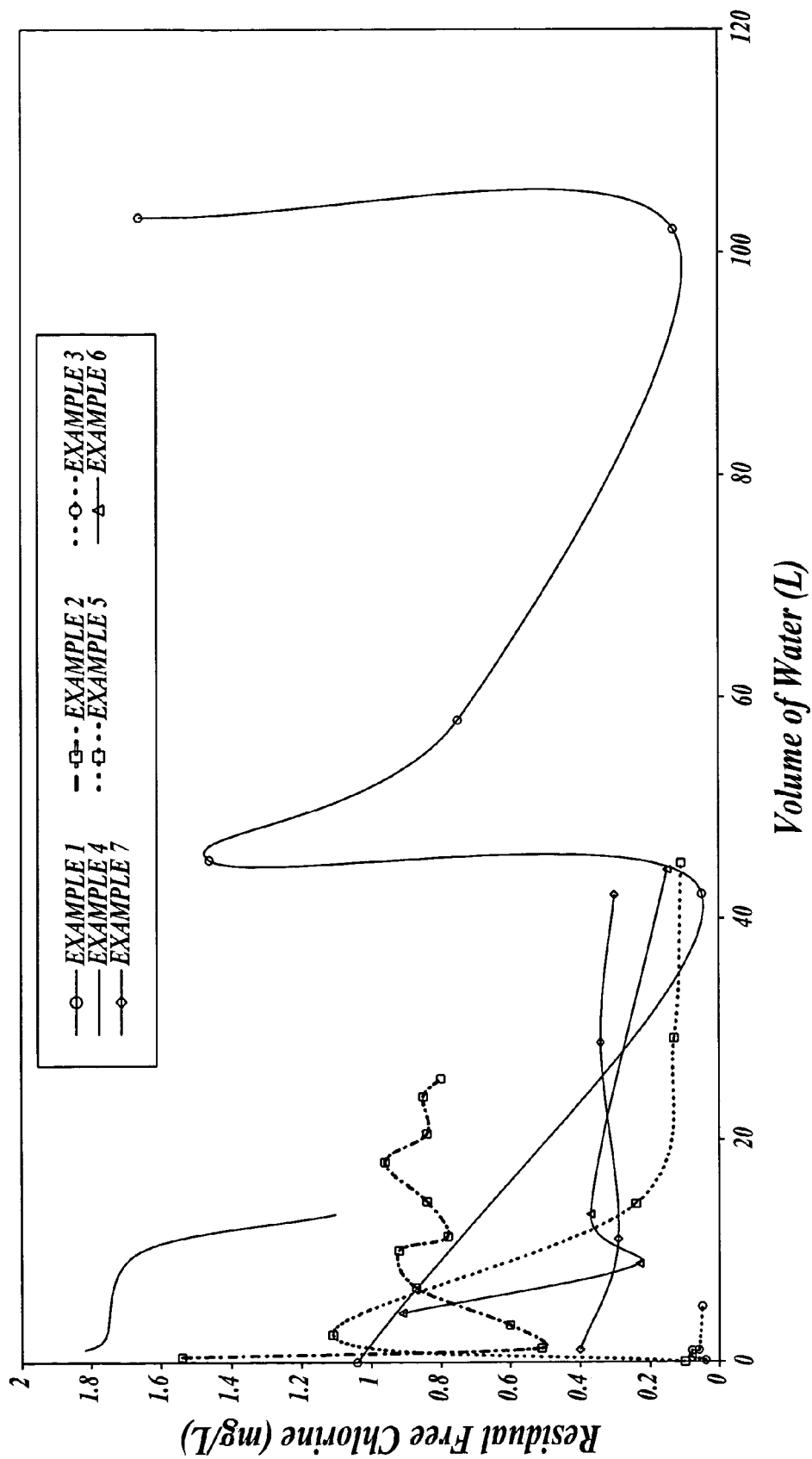
FIG. 3 is a graph illustrating the chlorine concentrations produced by articles made according to the present invention as plotted against cumulative water flow.
Figure 4:
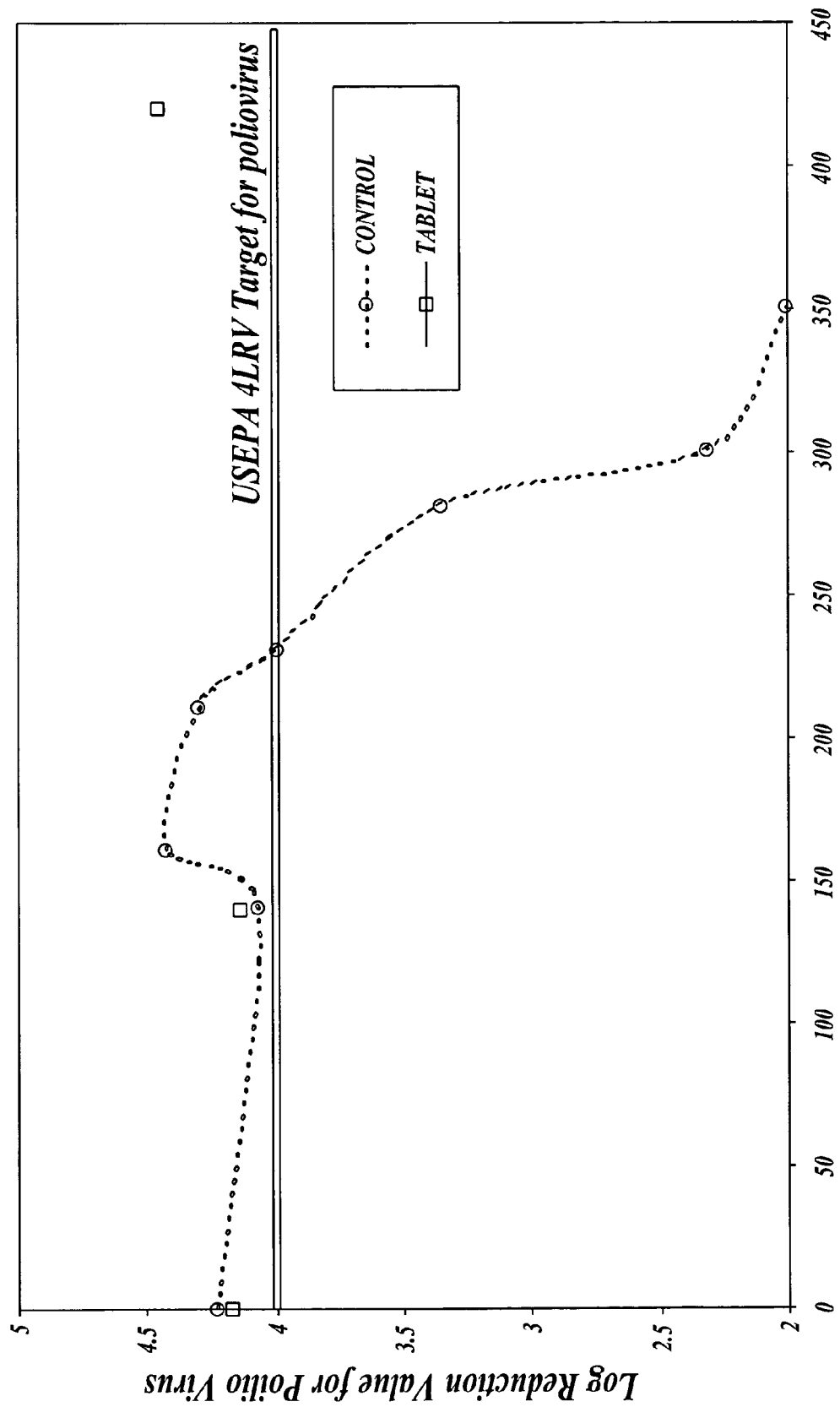
FIG. 4 is a graph illustrating the poliovirus LRV for both the control and the challenge system plotted against cumulative water flow.
Figure 5:
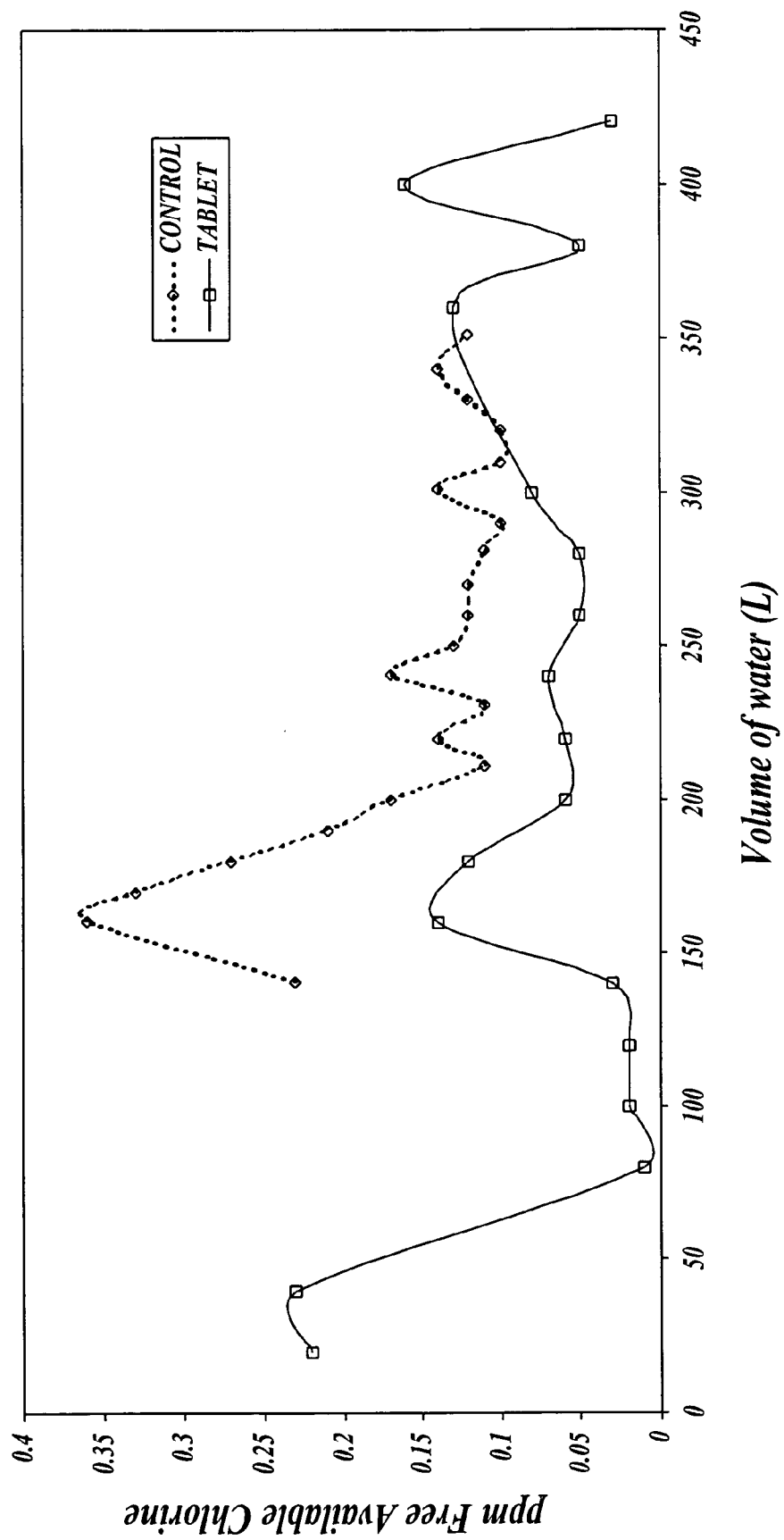
FIG. 5 is a graph illustrating the chlorine concentration produced by an article according to the present invention as plotted against cumulative water flow.

As the following examples demonstrate, a low halogen concentration in water made to contact PSH/HPSH polymer beads can create and maintain a halogen loading on the PSH/HPSH polymer sufficient for the polymer to maintain continuous biocidal activity to meet EPA standards, without having to be recharged. The concentrations of chlorine provided by representative examples of articles made in accordance with the invention are illustrated in FIG. 3. The chlorine concentrations shown in FIG. 3 are within the concentration range of about 0.1 ppm (weight) to about 3 ppm (weight) required to constantly sustain halogenated polystyrene beads having pendant hydantoin groups biocidally effective, but without effecting water potability. FIG. 3 shows a variety of elution profiles for a halogen from an article made in accordance with the invention. Representative halogen elution rate profiles include, but are not limited to a substantially constant profile, a rapid increase profile, a rapid decrease profile, a gradual increase profile, a gradual decrease profile, or a sinusoidal profile.

EXAMPLE 1

Sustaining Biocidal Efficacy of HPSH Beads With Diluted Bleach

Two beds arranged as shown in FIG. 1, each containing 20 g of chlorinated HPSH beads (16.9% wt/wt of Cl+ (Cl+ is the chlorine attached to a nitrogen on the hydantoin available for the biodemand)) and confirmed to be of a biocidal state achieving a 4-log reduction value (LRV) in poliovirus and a 6-LRV in *Klebsiella terrigena* (as determined using the methods described in the USEPA *Guide Standard and Protocol for Testing Microbiological Purifiers: Report of Task Force,* 1987), were challenged with feed water having the characteristics of 1,500 mg/L total dissolved solids as sea salts, 10 mg/L of total organic carbon as humic acid, and a pH of 9.0 adjusted using NaOH and HCl. Each bed was continuously challenged at 60 ml/min. One bed was designated the control and continuously challenged only with the feed water. The other bed was continuously challenged with feed water that was adjusted to 2 ppm free chlorine (as measured by N,N-diethylphenylenediamine (DPD) reagent using HACH Corp. Method 8021) using dilute sodium hypochlorite (i.e., bleach). After treating the beds with 140 L of the respective feed waters to the two beds, the weight percentage of chlorine (measured as Cl+) of the polymers in the beds was determined using an iodometric/thiosulfate titration of 1-gram of weighted crushed polymer. The polymer of the control bed was measured at 15.9% by weight chlorine, while the polymer of the test bed increased to a chlorine weight percentage of 17.2%. The chlorine concentration in the water is plotted as a function of cumulative water flow in FIG. 3.

EXAMPLE 2

Sustaining Biocidal Efficacy of HPSH Beads With Trichloromelamine and Magnesium Oxide Tablet A commercially available gravity feed ceramic drinking water system as shown in FIG. 2 (Doulton Berkefeld) was used along with a 20 gram cartridge of HPSH polymer (having 16% Cl+ wt/wt) attached to the outlet of the ceramic filter. The system was challenged with feed water having the characteristics of 1,500 mg/L total dissolved solids as sea salts, 10 mg/L of total organic carbon as humic acid, and a pH of 9.0 adjusted using NaOH and HCl. The system was allowed to run daily at 10 liters per day at an average flow rate of 10 ml/min using chlorine-free tap water and challenged weekly using the above challenge water until the poliovirus log reduction dropped below a complete kill of 4-LRV (as determined using the methods described in the USEPA *Guide Standard and Protocol for Testing Microbiological Purifiers: Report of Task Force*, 1987). Prior to the introduction of an article that releases a low-level of free chlorine, the poliovirus LRV was measured at 1.36-LRV. A compressed tablet of ½-inch diameter and having a mass of 800 mg (Parr Pellet Press, Parr Instruments Co.) and a density of 1.9895 g/cc of well mixed powdered trichloromelamine and magnesium oxide in a ratio of 1:1 by weight, was placed in situ above the inlet to the cartridge containing the PSH/HPSH polymer. Samples of the water coming into contact with the compressed tablet were taken prior to entering the cartridge and contained 0.30 ppm of free chlorine (as measured by N,N-diethylphenylenediamine (DPD) reagent using HACH Corp. Method 8021). The following week's challenge measured a poliovirus LRV at 4.26-LRV. The chlorine concentration in the water is plotted as a function of cumulative water flow in FIG. 3.

For examples 3–8, the sustainability of biocidal activity is demonstrated using PSH polymer (0% wt/wt of Cl+) to avoid the need of testing the LRV during each example. It was found that any level of biocidal activity of HPSH polymer can be sustained as long as the halogen loading on a PSH polymer is found to increase. Furthermore, the residual halogen level in the water remained within the ranges acceptable for drinking. A tablet that was found to both increase the weight percent of halogen in PSH polymer and also maintain the residual level of halogen within the ranges acceptable for drinking demonstrates a suitable formulation for a tablet according to the invention. The increase in the halogen weight percent represents the sustaining rate for the tablet for each of the examples.

EXAMPLE 3

Activating Biocidal Efficacy of PSH Beads With Trichloromelamine Tablet

Two beds, each containing 22 g of PSH polymer in bead form (0% wt/wt of Cl+) arranged as shown in FIG. 1, were challenged with municipally treated drinking water that was processed through an activated carbon block commonly sold into retail markets for the removal of chlorine taste and odor. The water contained less than 0.02 ppm of free chlorine and had a hardness of 0.07 ppm (as total $CaCO_3$ using HACH hardness method 8030). One bed was designated the control and continuously challenged only with the feed water. The other bed was continuously challenged with feed water that flowed over a solid ½-inch diameter, 550 mg, compressed tablet of compacted powdered trichloromelamine (Parr Pellet Press, Parr Instruments Co.) having a density of 1.3678 g/cc. The feed water after the pellet contained 0.10 ppm to about 0.30 ppm of free chlorine (as measured by N,N-diethylphenylenediamine (DPD) reagent using HACH Corp. Method 8021) and hardness as $CaCO_3$ was measured at 3.06–3.44 ppm. After treating the bed for 40 L of the respective feed waters at an average flow rate of 10 ml/min, the weight percentage of chlorine determined through iodometric/thiosulfate titration in the control bed was measured at 0.0% wt/wt, while the test bed increased to a chlorine weight percentage of 0.07%. The chlorine concentration in the water is plotted as a function of cumulative water flow in FIG. 3.

EXAMPLE 4

Activating Biocidal Efficacy of PSH Beads With Dichlorodimethylhydantoin, Sodium Metaphosphate and Teflon 7 Tablet Two beds each containing 1.65 g of PSH polymer in bead form (0% wt/wt of Cl+) arranged as shown in FIG. 1 were challenged with municipally treated drinking water that was processed through an activated carbon block commonly sold into retail markets for the removal of chlorine taste and odor. The water contained less than 0.02 ppm of free chlorine and had a hardness of 0.07 ppm (as total $CaCO_3$ using HACH hardness method 8030). One bed was designated the control and continuously challenged only with the feed water. The other bed was continuously challenged with feed water that flowed over a solid, ¼-inch diameter, 240 mg compressed tablet (Parr Pellet Press, Parr Instruments Co.) having a density of 2.388 g/cc of well mixed powdered dichlorodimethylhydantoin, sodium metaphosphate, and TEFLON 7® (DuPont) at a ratio of 2:2:1 by weight. The feed water after the pellet contained 1.10 ppm to 1.82 ppm of free chlorine (as measured by N,N-diethylphenylenediamine (DPD) reagent using HACH Corp. Method 8021) and hardness as $CaCO_3$ was measured at 0.16–3.26 ppm. After treating the bed for 13 L of the respective feed waters at an average flow rate of 222 ml per minute, the weight percentage of chlorine determined through iodometric/thiosulfate titration in the control bed measured 0.0% wt/wt, while the test bed increased to a chlorine weight percentage of 0.20%. The chlorine concentration in the water is plotted as a function of cumulative water flow in FIG. 3.

EXAMPLE 5

Activating Biocidal Efficacy of PSH Beads With Calcium Hypochlorite and Teflon 7 Tablet Two beds each containing 2.05 g of PSH polymer in the form of beads (0% wt/wt of Cl+) arranged as shown in FIG. 1 were challenged with municipally treated drinking water that was processed through an activated carbon block commonly sold into retail markets for the removal of chlorine taste and odor. The waters contained less than 0.02 ppm of free chlorine and had a hardness of 0.07 ppm (as total $CaCO_3$ using HACH hardness method 8030). One bed was designated the control and continuously challenged only with the feed water. The other bed was continuously challenged with feed water that flowed over a solid, ¼-inch diameter, 400 mg compressed tablet (Parr Pellet Press, Parr Instruments Co.) having a density of 3.980 g/cc of well mixed powdered of calcium hypochlorite and TEFLON 7® (DuPont) at a ratio of 1:3 by weight. The feed water after the pellet contained 0.11 to 0.80 ppm of free chlorine (as measured by N,N-diethylphenylenediamine (DPD) reagent using HACH Corp. Method 8021) and hardness as CaCO3 was measured at 2.51–3.12 ppm. After treating the bed for 45 L of the respective feed waters at an average flow rate of 250 ml per minute, the weight percentage of chlorine determined by iodometric/thiosulfate titration in the control bed measured 0.0% wt/wt, while the test bed increased to a chlorine weight percentage of 0.60%. The chlorine concentration in the water is plotted as a function of cumulative water flow in FIG. 3.

EXAMPLE 6

Activating Biocidal Efficacy of PSH Beads With Sodium Dichloroisocyanurate, Calcium Phosphate and Teflon 7 Tablet Two beds each containing 2.0 g of PSH polymer in bead form (0% wt/wt of Cl+) arranged as shown in FIG. 1 were challenged with municipally treated drinking water that was processed through an activated carbon block commonly sold into retail markets for the removal of chlorine taste and odor. The water contained less than 0.02 ppm of free chlorine and had a hardness of 0.07 ppm (as total $CaCO_3$ using HACH hardness method 8030). One bed was designated the control and continuously challenged only with the feed water. The other bed was continuously challenged with feed water that flowed over a solid, ¼-inch diameter, 200 mg compressed tablet (Parr Pellet Press, Parr Instruments Co.) having a density of 1.990 g/cc of well mixed powdered sodium dichloroisocyanurate, calcium phosphate dibasic and TEFLON 7® (DuPont) in a ratio of 1:1:2 by weight. The feed water after the pellet contained 0.91 to 3.4 ppm of free chlorine (as measured by N,N-diethylphenylenediamine (DPD) reagent using HACH Corp. Method 8021) and hardness as CaCO3 was measured at 0.76–2.97 ppm. After treating the beds with 44 L of the respective feed water at a flow rate of 222 ml per minute, the weight percentage of chlorine by iodometric/thiosulfate titration in the control bed measured 0.0% wt/wt, while the test bed increased to a chlorine weight percentage of 0.30%. The chlorine concentration in the water is plotted as a function of cumulative water flow in FIG. 3.

EXAMPLE 7

Activating Biocidal Efficacy of PSH Beads With Trichloroisocyanurate, Sodium Metaphosphate and Teflon 7

Two beds each containing 2.09 g of PSH polymer in bead form (0% wt/wt of Cl+) arranged as shown in FIG. 1 were challenged with municipally treated drinking water that was processed through an activated carbon block commonly sold into retail markets for the removal of chlorine taste and odor. The water contained less than 0.02 ppm of free chlorine and had a hardness of 0.07 ppm (as total $CaCO_3$ using HACH hardness method 8030). One bed was designated the control and continuously challenged only with the feed water. The other bed was continuously challenged with feed water that flowed over a solid, ¼-inch diameter, 200 mg, compressed tablet (Parr Pellet Press, Parr Instruments Co.) having a density of 1.990 g/cc of well mixed powdered sodium trichloroisocyanurate, sodium metaphosphate and TEFLON 7® (DuPont) at a ratio of 1:0.5:2 by weight. The feed water after the pellet contained 0.30 to 0.76 ppm of free chlorine (as measured by N,N-diethylphenylenediamine (DPD) reagent using HACH Corp. Method 8021) and hardness as CaCO3 was measured at 1.59–3.16 ppm. After treating the beds with 34 L of the respective feed water at an average flow rate of 180 ml per minute, the weight percentage of chlorine by iodometric/thiosulfate titration in the control bed measured 0.0% wt/wt, while the test bed increased to a chlorine weight percentage of 0.30%. The chlorine concentration in the water is plotted as a function of cumulative water flow in FIG. 3.

EXAMPLE 8

Activating Biocidal Efficacy of PSH Beads With Dibromo-5,5-Dimethylhydantoin Tablet Two beds each containing 2.00 g of PSH polymer in bead form (0% wt/wt of Cl+) arranged as shown in FIG. 1 were challenged with municipally treated drinking water that was processed through an activated carbon block commonly sold into retail markets for the removal of chlorine taste and odor. The water contained less than 0.02 ppm of free chlorine and had a hardness of 0.07 ppm (as total $CaCO_3$ using HACH hardness method 8030). One bed was designated the control and continuously challenged only with the feed water. The other bed was continuously challenged with feed water that flowed over a solid, ¼-inch diameter, 200 mg, tablet (Parr Pellet Press, Parr Instruments Co.) having a density of 1.990 g/cc composed of commercially available nuggets of dibromo-5,5-dimethylhydantoin (ALBROM 100, Albemarle Corp.) crushed and reconstituted to have the parameters above. The feed water after the pellet contained 0.62 to 4.13 ppm of total bromine (as measured by N,N-diethylphenylenediamine (DPD) reagent using HACH Corp. Method 8021) and hardness as $CaCO_3$ was measured at 0.70–1.93 ppm. After treating the bed for 46 L of the respective feed waters at an average flow rate of 192 ml per minute, the weight percentage of bromine (Br+) determined by iodometric/thiosulfate titration in the control bed measured 0.0% wt/wt, while the test bed increased to a bromine weight percentage of 1.20%.

EXAMPLE 9

Sustaining Biocidal Efficacy of HPSH Beads With Trichloromelamine, Sodium Hexametaphosphate and Sodium Bicarbonate Tablet Two commercially available gravity feed ceramic drinking water systems as shown in FIG. 2 (Doulton Berkefeld) were used along with a 20 gram cartridge of HPSH polymer (having 14% Cl+ wt/wt) attached to the outlet of the ceramic filter. The systems were challenged with feed water having the characteristics of 1,500 mg/L total dissolved solids as sea salts, 10 mg/L of total organic carbon as humic acid, and a pH of 9.0 adjusted using NaOH and HCl. The systems were allowed to run daily at 10 to 20 liters per day at an average flow rate of 15 ml/min using chlorine-free tap water and challenged periodically using the above challenge water to measure poliovirus log reduction as determined using the methods described in the USEPA *Guide Standard and Protocol for Testing Microbiological Purifiers: Report of Task Force,* 1987. One unit was designated as the control while the other unit contained a compressed tablet of ½-inch diameter and having a mass of 550 mg (Parr Pellet Press, Parr Instruments Co.) and a density of 1.52 g/cc of well mixed powdered trichloromelamine, sodium hexametaphosphate and sodium bicarbonate in a ratio of 2:1:0.20 by weight, placed in situ above the inlet to the cartridge containing the PSH/HPSH polymer. The above tablet dissolved within and was replaced with a fresh tablet after 70 L, 140 L, 210 L, 280 L, 350 L, and 420 L had passed through the system. The control unit showed a drop in poliovirus LRV from above 4 to 3.5 at 280 liters. The drop in poliovirus LRV continued down to 2.5 LRV by 351 L. The challenge unit containing the in-situ compressed tablet, on the other hand, continued to show a greater than 4 LRV through 420 L. The poliovirus LRV for both the control and challenge system is plotted as a function of total water through the system in FIG. 4. Samples of the water coming into contact with the compressed tablet system and control system were taken after the PSH/HPSH bead bed and contained 0.05 to 0.36 ppm of free chlorine (as measured by N,N-diethylphenylenediamine (DPD) reagent using HACH Corp. Method 8021). The chlorine concentration in the water leaving the PSH/HPSH bead beds for both the control and challenge systems is plotted as a function of cumulative water flow in FIG. 5.

It can be seen from the above examples that using low concentrations of chlorine and/or bromine can halogenate HPSH polymers to a level sufficient to be effective biocides.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for sustaining the biocidal activity of halogenated polystyrene hydantoin beads, comprising:

incorporating a halogen source into water being treated with halogenated polystyrene hydantoin beads to provide treated water suitable for drinking, wherein the halogen source provides a free halogen concentration from about 0.1 ppm to about 10 ppm in the water, the concentration being sufficient to maintain the biocidal activity of the halogenated polystyrene hydantoin beads.

2. The method of claim 1, wherein halogenated polystyrene hydantoin beads comprise chlorinated polystyrene hydantoin beads.

3. The method of claim 1, wherein halogenated polystyrene hydantoin beads comprise brominated polystyrene hydantoin beads.

4. The method of claim 1, wherein the halogen concentration is about 0.1 ppm to about 4 ppm.

5. The method of claim 1, wherein the water to be treated is continuously supplied to the beads.

6. A method for halogenating a polymer having pendent hetrocyclic N-halamine groups, comprising:

flowing water from a first compartment containing a composition comprising at least one halogen source to a second compartment containing a polymer having pendent hetrocyclic N-halamine groups; wherein the halogen source provides a free halogen concentration from about 0.1 ppm to about 10 ppm in said flowing water.

7. The method of claim 6, wherein the composition supplies a continuous concentration of free halogen.

8. The method of claim 7, wherein the concentration of free halogen is from about 0.1 ppm to about 4 ppm.

9. The method of claim 6, wherein the polymer having pendent hetrocyclic N-halamine groups comprises N-halo-hydantoinyl groups.

10. The method of claim 6, wherein the halogen is chlorine.

11. The method of claim 6, wherein the halogen is bromine.

* * * * *

UNITED STATES PATENT AND TRADEMARK OFFICE
CERTIFICATE OF CORRECTION

PATENT NO. : 7,014,781 B2  Page 1 of 1
APPLICATION NO. : 11/180280
DATED : March 21, 2006
INVENTOR(S) : M.A. Bridges et al.

It is certified that error appears in the above-identified patent and that said Letters Patent is hereby corrected as shown below:

| COLUMN | LINE | ERROR |
|---|---|---|
| (56) Pg. 2, col. 2 | Refs. Cited (U.S. Pats., Item 29) | "Quincy" should read --Quincy, Ill-- |
| 16 (Claim 6, | 15-16 lines 1-2) | "pendent hetrocyclic" should read --pendant heterocyclic-- |
| 16 (Claim 6, | 20 line 6) | "pendent hetrocyclic" should read --pendant heterocyclic-- |
| 16 (Claim 6, | 22 line 8) | "said flowing water" should read --the flowing water-- |
| 16 (Claim 9, | 29 line 2) | "pendent hetrocyclic" should read --pendant heterocyclic-- |

Signed and Sealed this

Eighth Day of August, 2006

JON W. DUDAS
*Director of the United States Patent and Trademark Office*